United States Patent [19]

Strub

[11] Patent Number: 5,285,674
[45] Date of Patent: Feb. 15, 1994

[54] MEASUREMENT DEVICE FOR DETECTING GAS CHARGE OF A PLASTIC COMPONENT

[75] Inventor: Fritz Strub, St. Gallen, Switzerland

[73] Assignee: Spuhl AG, Gallen, Switzerland

[21] Appl. No.: 900,871

[22] Filed: Jun. 18, 1992

[30] Foreign Application Priority Data

Jun. 18, 1991 [DE] Fed. Rep. of Germany ....... 4119966

[51] Int. Cl.[5] .............................................. G01N 7/00
[52] U.S. Cl. .................................... 73/19.01; 73/19.1
[58] Field of Search ........................... 73/19.01, 19.1; 521/917

[56] References Cited

U.S. PATENT DOCUMENTS

| | | | |
|---|---|---|---|
| 3,946,228 | 3/1976 | Biermann | 73/19.01 |
| 4,329,869 | 5/1982 | Toda | 73/19.1 |
| 4,365,505 | 12/1982 | Hölzl | 73/19.1 |
| 4,376,172 | 3/1983 | Belangee et al. | 521/917 |
| 4,448,902 | 5/1984 | Coblenz et al. | 521/917 |
| 4,862,729 | 9/1989 | Toda et al. | 73/19.05 |
| 4,948,815 | 3/1990 | Krippl et al. | 521/50 |
| 4,973,608 | 8/1990 | Krippl et al. | 521/50 |
| 5,000,882 | 3/1991 | Proksa et al. | 521/917 |
| 5,020,359 | 6/1991 | Castel | 73/19.1 |

FOREIGN PATENT DOCUMENTS

| | | |
|---|---|---|
| 2929013A1 | 5/1981 | Fed. Rep. of Germany . |
| 3045456A1 | 7/1982 | Fed. Rep. of Germany .. |
| 3021255C2 | 2/1985 | Fed. Rep. of Germany . |
| 3132597C2 | 4/1985 | Fed. Rep. of Germany . |
| 3336037A1 | 6/1985 | Fed. Rep. of Germany . |
| 3434444A1 | 2/1986 | Fed. Rep. of Germany . |
| 3830209A1 | 4/1990 | Fed. Rep. of Germany . |

*Primary Examiner*—Robert J. Warden
*Assistant Examiner*—Laura E. Collins
*Attorney, Agent, or Firm*—Robbins, Berliner & Carson

[57] ABSTRACT

For measuring the air charge of a plastic component for a low-pressure multicomponent foam system, the gas-charged plastic component is admitted into a measuring chamber. The gas pressure of the plastic component displaces a measuring piston in the measuring chamber and the displacement distance of the piston is a measure of the gas charge.

4 Claims, 3 Drawing Sheets

MEASUREMENT DEVICE FOR DETECTING GAS CHARGE OF A PLASTIC COMPONENT

BACKGROUND OF THE INVENTION

The present invention relates to a measurement arrangement for detecting the gas charge of a plastic component.

In foam systems as described herein, it is known that an A-component (e.g., polyol) is kept under controlled pressure in a component container. A second component (the B-component), which has a circuit identical to that described below for the A-component, is present. The two components are introduced together into a mixer head and then applied to a workpiece by injection through an injection head, whereby the air contained in the A-component is the determining factor for the porosity of the injection molded plastic article. It is also possible that the B-component may unintentionally contain air which can then also have an effect on the foam.

Such a plastic article is preferably a seal, which is sprayed with the abovementioned system onto a workpiece and then reacts chemically, whereby the seal foams and then hardens.

Until now, there existed the problem that the air portion in the A-component could be kept uniform only with difficulty, since until now it was known to blow this air into the A-component container, mixing it as intimately as possible with this A-component through the action of a stirring device.

Since the interior of the component container is under pressure and the air is introduced into the A-component in fine beads under higher pressure, the air bonds to the A-component. This A-component mixture combined with air is fed to the mixing head via a material outlet and a dosing pump.

It is also known to provide the B-component with an identical circuit, consisting of a component container, material outlet, dosing pump, and inlet into the mixing head, with no air added to the B-component, although it may contain air.

As already mentioned, it was, until now, difficult to regulate the amount of air in the component container such that a uniform percentage of air was always maintained in the A-component regardless of the fullness of the component container.

It has previously been known to detect the amount of air in the A-component by means of a measuring arrangement disposed in the outlet of the A-component container.

The measuring principle of this measuring arrangement was based on the fact that the liquid to be measured was introduced into a measuring chamber, in which measuring chamber a sound generator and sound receiver were present. By bombarding the volume to be measured with sound, a certain attenuation of the sound waves was generated due to the air contained in the A-component, which attenuation was detected by the sound receiver. By evaluating the attenuation, it was possible to determine the proportion of air in the A-component. However, a disadvantage of the known measuring arrangement is that the cost of measurement is unreasonably high and such a device is very expensive to produce and to service.

The object of the present invention is therefore to improve a measurement arrangement of the type mentioned in the introduction such that it is significantly more cost-effective to produce, operates more reliably, and assures fast monitoring of the air contained in the A-component.

SUMMARY OF THE INVENTION

The solution is achieved through a measurement arrangement as described herein, according to which it is essential that the measuring arrangement is disposed in the outflow tube of the component container and a valve opens and closes the measurement chamber, with the measurement chamber consisting of a measuring piston, which is disposed movably in a measuring space as a displacement piston, and that the displacement distance of the measuring piston in the measurement chamber is detected by a distance sensor.

BRIEF DESCRIPTION OF THE DRAWINGS

In the following, the invention is explained in greater detail using drawings depicting only one embodiment. In this process, additional characteristics and advantages essential to the invention arise from the drawings and their description, in which.

DETAILED DESCRIPTION OF THE INVENTION

Figure 1:
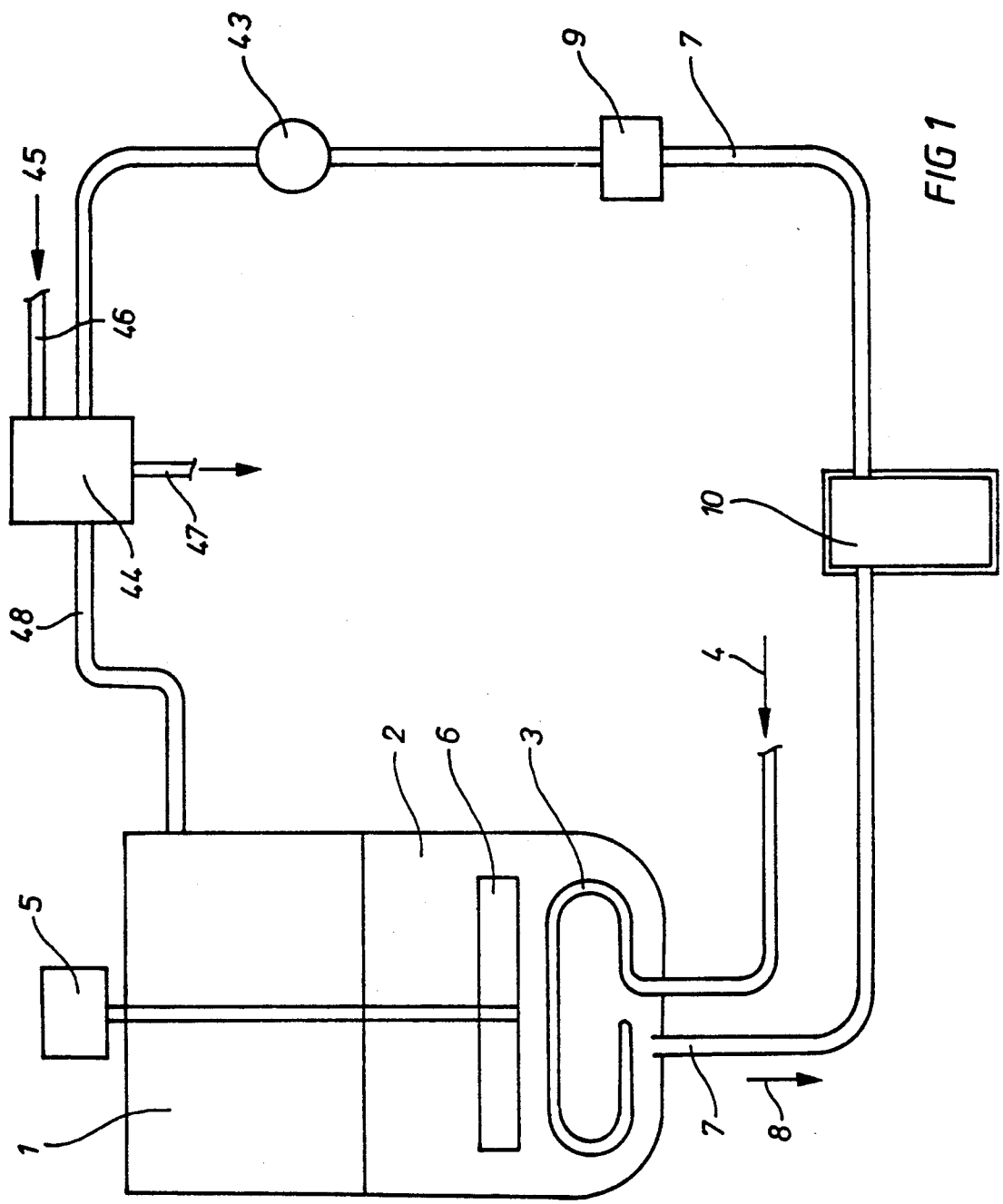
FIG. 1 is a schematic diagram of a circuit for the A-component.

An essential characteristic of the present invention is that the measuring arrangement is disposed in the outflow tube of the component container and that an accurately predefined charge of the component charged with air can be introduced into a measuring space with the help of a valve. As soon as the measuring space is filled, it is sealed against further penetration of the component charged with air and the measurement begins.

Before the beginning of the measurement, the measuring piston was held by means of a counterforce (e.g., a spring or an electromagnet) in the raised position in its displacement position in the measuring space.

In a design with a roller membrane, the lifting of piston must result from air pressure, so that the membrane cannot collapse. The spring moves downward such that the pressure under the piston is always higher than above the roller membrane (with the exception of the lowest extreme position, where the membrane is supported).

The forces to raise the piston are very high (e.g., with a 5 bar component pressure: approximately 700N). This is hardly possible with an electromagnet.

After the beginning of measurement, this counterforce is removed and the piston is displaced downward by the air-charged components penetrating into the measuring space. The upward counterforce must be reduced slowly until the piston begins to move slowly downward. The pressure must not drop in the A-component until the ball valve closes (flow resistance of the A-component).

Since the air-charged A-component flows into the outflow tube at a pressure in the range from 2 to 10 bar, the measuring space is also filled under this pressure with this air-charged component and then sealed from above by the valve such that no additional component can continue to flow in.

Through the closing of the valve and the downward displacement of the measuring piston, a relief of the pressure in the measuring space occurs, whereby the pressure initially in the range from 2 to 10 bar drops to a significantly lower value. Due to this expansion in the measuring space, the A-component begins to give off gas and releases the air into the measuring space in the form of beads of air, resulting in further downward displacement of the measuring piston in the direction of its lengthwise axis. This displacement of the piston due to the escaping air is used to measure the air content of the measuring space.

The additional displacement distance of the piston due to the component giving off gas is detected by measuring the displacement distance of the piston. For this, it is preferable if the lengthwise movement of the measuring piston is detected by an electrical proximity switch. It is thus possible to provide that a plug gage, which is opposite a proximity switch, be applied to the lower end of the piston rod of the measuring piston. The plug gage thus approaches the proximity switch disposed in the bottom region of the measuring arrangement with the increasing escape of gas from the A-component. The approach of this plug gage to the proximity switch is a measure of the air content of the liquid in the measuring chamber.

If the liquid is not charged with air, there is no approach of the plug gage to the proximity switch and this is sent as a signal to introduce more air into the component container. As soon as the next charge is introduced into the measuring chamber for the next measurement, there is a release of the air in the measurement chamber and the piston is displaced downward because of this increased volume and the plug gage thus approaches the proximity switch. The travel of the plug gage toward the proximity switch is thus directly proportional to the amount of air which is contained in the measuring space of the A-component delivered.

Thus, the air content of the A-component can be relatively accurately determined, through continued successive measurements, whereby in successive measuring cycles, a specific charge is always taken from the A-component.

Such an arrangement is very cost-effective since no electronic sound converter and sound generator are needed; instead, only a simple measuring piston is needed in conjunction with a measuring space, which is sealed at the bottom by a pot membrane.

In order to hold the measuring piston in its raised non-measuring position, it is preferable if the measuring piston is held in its raised position from below by compressed air, in order to clear the measuring space by displacement of the component.

It is also preferable if the valve which causes flow of the air-charged A-component into the measuring space is activated directly by the measuring piston itself. This yields a particularly simple design since in the raised displacement position of the measuring piston, a ball valve is closed by a piston rod of the measuring piston such that the A-component can flow in and then out again through a flow-through bore in the measurement arrangement, but because of the closed position of this ball valve, the A-component cannot flow into the measuring space.

As soon as the counterforce is removed from the measuring piston, the piston is displaced downward due to the existing pressure from above (from the A-component), whereby the ball valve opens simultaneously and the liquid flows into the measuring space. Simultaneously the ball valve is carried along with it and then comes to rest on a lower valve seat, whereby additional flow of the liquid into the measuring space is prevented. The measuring space is thus filled with air-charged liquid, and the actual measurement of the air contained in it can begin.

There is no valve seat for the ball in the upper position.

Since the measuring space is closed from above by the ball valve and the measuring piston moves downward, a drop in pressure occurs in the measuring space, resulting in the above described release of gas from the liquid and the volume in the measuring space increasing again, such that the measuring piston is displaced downward and the proximity switch reacts to it.

DESCRIPTION OF PREFERRED EMBODIMENTS

The measurement principle described can be modified for use in various embodiments. In a first embodiment, it is possible to provide that the previously described ball valve activated directly by the measuring piston can be activated by its own control. Such a control can be either an electromagnetic control or a compressed air control.

In another embodiment, it is possible to provide that the raised position of the measuring piston is not obtained with compressed air; instead, an electromagnet generates this counterforce.

In this case no roller membrane (virtually free of friction) can be used. The roller membrane would collapse (damage to the membrane as well as volume errors).

The object of the present invention does not result solely from the object of the individual claims, but also from the combination of the individual claims among each other. All data and characteristics disclosed in the documents including the abstract, and in particular, the spatial design depicted in the drawings are claimed as essential to the invention, to the extent that they are new, individually or in combination, compared to the prior art.

According to FIG. 1, a so-called A-component is contained in a component container 1, which component consists, for example, of the chemical material Polyol (registered trademark of the DuPont company). Polyol is a polyisocyanate.

Thus, the A-component is contained as the material 2 in the component container 1 and is stirred by a stirring device 6.

The interior of the component container 1 is kept constantly under a specific pressure. This pressure can be within the range from 2 to 10 bar; preferably it is 6 bar.

Below the stirring device 6, in the direction of the arrow 4, air is blown into the component container 1 via an air diffuser 3, with the air diffused in the form of fine beads into the material 2 via appropriate bores in the air diffuser 3.

The component thus charged with air is fed via an outlet 7 in the direction of the arrow 8 into a measuring arrangement 10. The measuring arrangement is explained later with reference to FIGS. 2 and 3.

In the connection to the measuring arrangement, a filter 9 is possibly disposed in the tube, behind which filter 9 a dosing pump 43 is disposed.

The dosing pump 43 delivers the air-charged A-component into a mixing head 44, where a B-component 46 is simultaneously introduced in the direction of the arrow 45. As already mentioned in the introduction, the B-component has a circuit identical to that illustrated in FIG. 1, but with the exception, that no air is blown in.

An injection head 47 is disposed on the mixing head 44, via which injection head the mixed A-B-component is applied to a workpiece.

At the outlet of the mixing head 44, a recirculation tube 48 is disposed, via which the unused A-component is returned to the component container 1.

The objective now is to obtain a relatively uniform charge of air in the A-component, in order to assure the most uniform foaming of the A+B mixed components possible in the injection head 47 on the workpiece.

For this, the introduction of air in the direction of the arrow 4 must be regulated.

The measuring arrangement 10 is used to detect the amount of the charge of air in the A-component.

Figure 2:
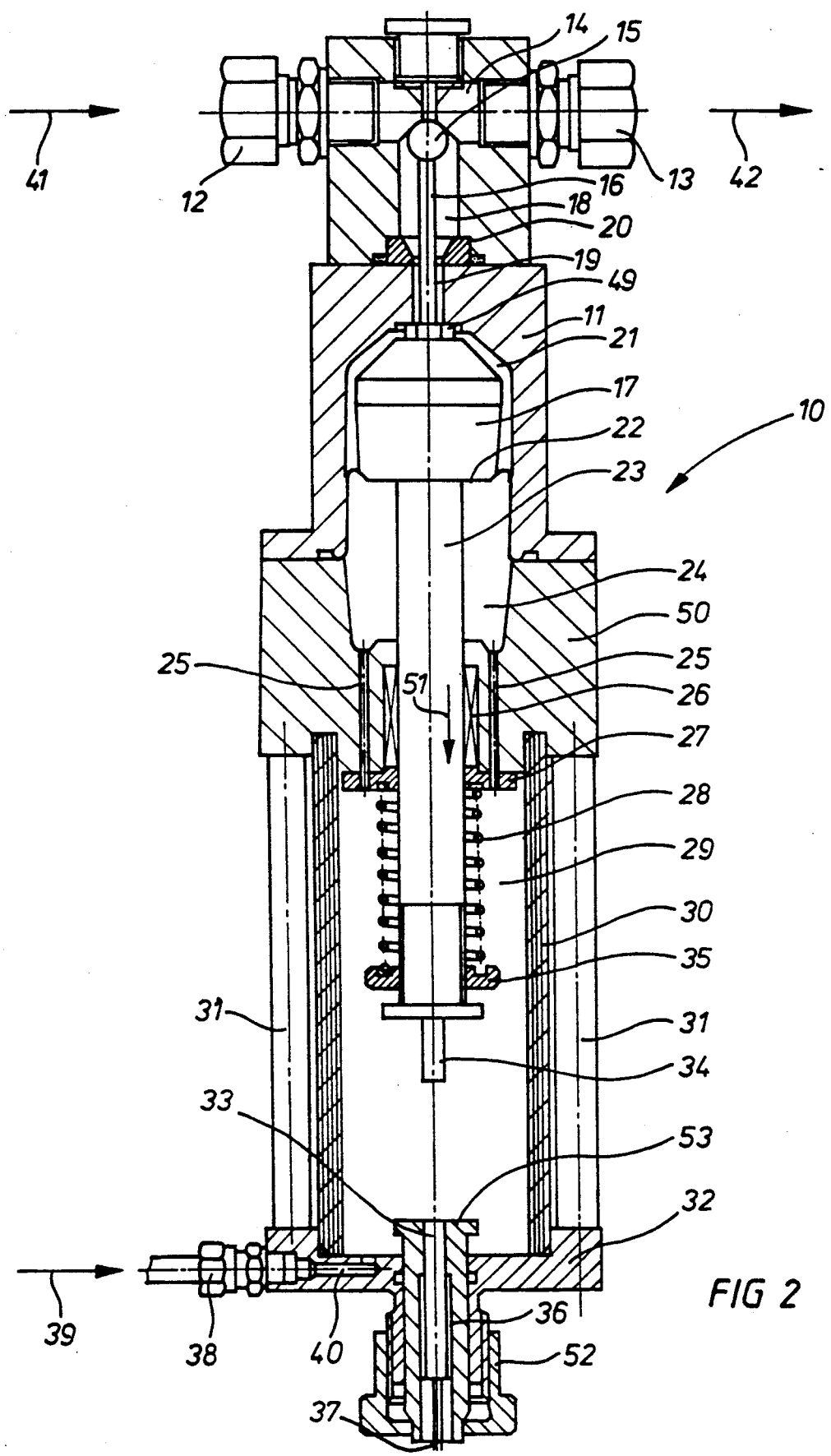
FIG. 2 illustrates the measuring arrangement in cross-section in the non-measuring position.

The A-component is admitted into the measuring arrangement 10 via an inlet nozzle 12 and exits the outlet nozzle 13 in the direction of the arrow 42 in flowthrough operation via a flowthrough bore 14 (See FIG. 2).

Thus, in this non-measuring position the measuring arrangement according to FIG. 2 is not in operation.

The measuring arrangement consists essentially of a base 11, with a lower channel 18 branching off from the flowthrough bore 14.

In the open position, a ball valve 15 is held in the open position by a piston rod 16 of a measuring piston 17 such that the material of the A-component continues to flow into the channel 18 and also in a channel 19 underneath it.

There is no valve seat. This would cause interference. A passage 49 of approximately 2 mm is always present. The upward movement of the piston is restricted by hitting the ball.

On the other side, the measuring space 21 is bounded by a pot membrane 22, which is held so as to be leakproof in appropriate housing-proof ring grooves in the housing between the base 11 and the upper part 50.

A cylindrical bore 24 is disposed on the bottom of the pot membrane 22, which bore is connected via channel 25 with a lower bore 29 which allows the passage of air.

A piston rod 23 is attached on the bottom of the measuring piston 17, which rod is held so it can be displaced in the upper part 50 via longitudinal ball bearings 26. The longitudinal ball bearings 26 provide for easy displacability of the piston rod 23 in the upper part 50.

There is a spring 28, which is supported on one end housing-proof against a ring 27 in the housing and on its other end against a ring 35, which is attached on the piston rod 23 so it can be screwed on by threads. The spring 28 is not used to overcome friction (this is insignificantly low). The spring 28 generates a negative pressure of approximately 0.5 bar, for example, in the measuring space. The negative pressure promotes the release of gas in the measuring space, increases the volume of the air beads, and thus increases the measuring movement of the piston. The negative pressure is adjustable by means of the ring 35.

The spring 28 is very strong, for example, approximately 90N. It also holds the membrane under constant tension. Thus there is no volume error.

In this manner, the initial tension of the spring 28 can be adjusted by rotating the ring 35.

A plug gage 34 is applied on the lower end of the piston rod 23, which is positioned housing-proof in the housing in a base 32 of the measuring arrangement opposite a proximity switch 33. This proximity switch 33 is known and operates preferably according to an electronic measurement principle.

Here, it is important that the proximity switch 33 is moveable and anchorable in the direction of its lengthwise axis by means of a union nut 52, such that the measuring surface 53 of the proximity switch 33 can be adjusted inwardly and outwardly in a specific range in the bore 29.

Thus the proximity switch 33 can be calibrated as will be explained later with reference to FIG. 3.

Compressed air is also admitted into the bore 29 through an inlet 38 in the direction of arrow 39 via the bore 40, with this compressed air having a higher pressure than the pressure of the A-component.

Thus the measuring piston 17 is held in its raised position in the measuring chamber 21. The valve seat 20 is opened.

To enable observation of the entire measuring arrangement from the outside, it is preferable that the wall 30 be made of a transparent plastic material and, for simple disassembly of the entire arrangement, it is further preferable that the base 32 be attached by appropriate bolts 31 to the upper part 50.

Figure 3:
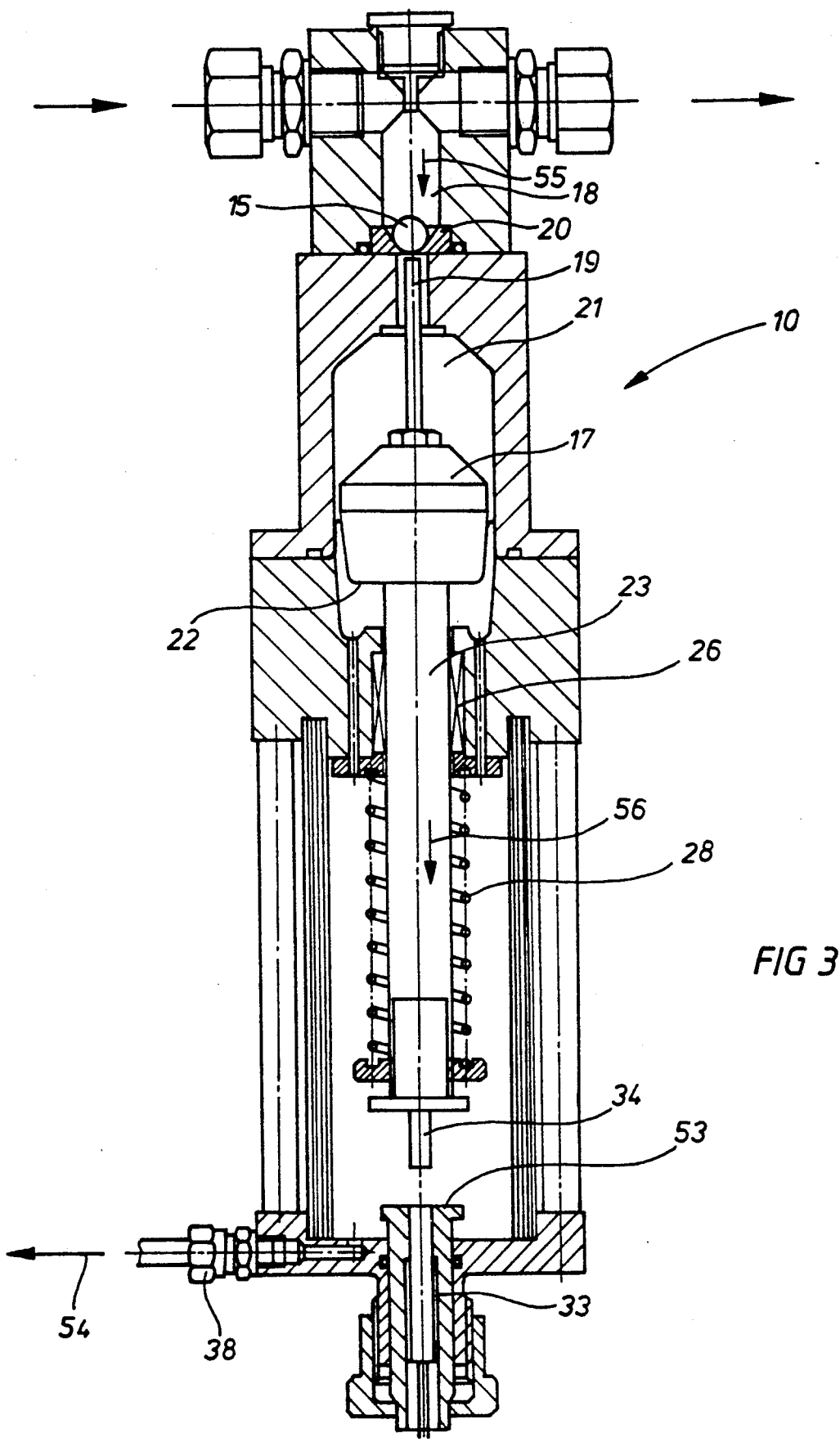
FIG. 3 illustrates the measuring arrangement according to FIG. 2 in the measuring position.

A measuring cycle according to FIG. 3 is now initiated as follows.

The compressed air, which was previously introduced into the bore 29 in the direction of arrow 39, is now removed (in the direction of arrow 54), such that now the counterforce against the pot membrane 22 is no longer present and the A-component flows into the measuring space 21 in the direction of the arrow 55 via the channel 18 and the still open valve seat 20, whereby the measuring piston 17 is simultaneously displaced downward in the direction of the arrow 55. Thus, the spring 28, which has relatively high spring resiliency, is relieved. It provides for a slow drop until the ball valve closes.

Specifically, the counterforce against the pot or roller membrane is also slowly reduced by the outflow of the air. The piston drops, with the pressure remaining constant in the measuring space.

As soon as the piston rod 19 comes to rest below the valve seat 20, the ball valve 15 seals the valve seat 20, such that no further component can flow into the measuring space 21 in the direction of the arrow 55. The measuring space 21 is thus filled with a precisely predefined charge of the air-charged liquid.

Due to the fact that the counterpressure against the pot membrane 22 is no longer present, a depressurization occurs in the measuring space 21 and the air-charged liquid contained therein begins to release gas, that is, depressurization down to below 1 bar absolute is obtained to approximately 0.5 bar (downward movement with the help of the spring resiliency).

The valve piston depicted the displacement position in FIG. 3 is thus displaced farther downward in the direction of the arrow 56 due to the increasing volume of air, whereby the plug gage 34 approaches the measuring surface 53 of the proximity switch 33.

After a specific measurement period, on the order of some seconds, no additional release of gas from the air-charged liquid in the measuring space 21 occurs, such that the plug gage 34 has assumed its final position opposite the measuring surface 53. This position is now detected by measurement technology via the proximity switch 33 and this signal is displayed to permit deriving an indication for charging the A-component with air.

Naturally, this signal can also be used later to regulate the introduction of air into the air diffuser 3 in the direction of the arrow 4, providing a control system in a known manner.

Consequently, this yields a closed control circuit. A proximity switch is provided. Thus no distance is measured with the signal "ON-OFF" (at approx. 1 mm distance, for example). The switching point is adjusted by means of the nut 52.

The plug gage 34 can be sunk into the piston rod 23 to reduce damage to the proximity switch and possibly to the roller membrane.

A control circuit is only possible with consecutive repetition of the measurement. Protection against too little air, and also against too much air, is important.

For example, measurement is performed for each charge such that slight air-charging of the material 2 is first undertaken and then a first measurement performed, whereby as a rule it is determined that the plug gage 34 does not adequately approach the measuring surface 53 of the proximity switch 33, such that the proximity switch 33 issues no measurement signal. Only after additional air is introduced into the air diffuser 3 in the direction of the arrow 4 is there increased air-charging of the A-component; and with the next measurement of the next charge a stronger release of gas from the air-charged component in the measuring space 21 takes place, and the plug gage 34 will approach the measuring surface 53 at a closer distance, such that now the proximity switch 33 responds and indicates that an adequate air-charge has been obtained.

In the event of too great a charging of the A-component with air, a limit value switch which indicates this excessive air-charging can also be present (maximum displacement of the piston rod 23 in the direction of the arrow 56), and then appropriate countermeasures can be introduced to prevent this excessive air-charging. Since material is used, the air content automatically drops when the air-charging is turned off.

The measurement must occur at adequately short time intervals such that no overcharging can occur.

Here, it is important that measurement be discontinuous, i.e., measurement by charge of the air-charged A-component, with it possible to perform such measurements in very rapid succession.

The present measuring arrangement is very sensitive and can also detect extremely small amounts of escaping air in the measuring space 21. The above-mentioned spring 28 is provided to increase sensitivity. The spring 28 is very strong and thus increases the sensitivity.

The release of gas in fact requires some time and stimulation from the negative pressure.

After completion of the measurement according to FIG. 3, a new measuring cycle is initiated by compressed air again being introduced through the inlet 38 in the direction of the arrow 39.

The measuring piston 17 is thus displaced upward in the direction opposite that depicted by the arrow 56 and again displaces the component from the measuring space 21 via the now opening ball valve 15 into the channel 18, where it is fed back into the circuit via the bore 14.

The following is a key to the drawings: 1. Component container; 2. Material; 3. Air diffuser; 4. Arrow direction; 5. Motor; 6. Stirring device; 7. Outlet; 8. Arrow direction; 9. Filter; 10. Measuring arrangement; 11. Base; 12. Inlet nozzle; 13. Outlet nozzle; 14. Flow-through bore; 15. Ball valve; 16. Piston rod; 17. Measuring piston; 18. Channel; 19. Channel; 20. Valve seat; 21. Measuring space; 22. Pot membrane; 23. Piston rod; 24. Cylinder bore; 25. Channel; 26. Longitudinal ballbearings; 27. Ring; 28. Spring; 29. Bore; 30. Wall; 31. Bolt; 32. Base; 33. Proximity switch; 34. Plug gage; 35. Ring; 36. Threads; 37. Connection; 38. Inlet; 39. Arrow direction; 40. Bore; 41. Arrow direction; 42. Arrow direction; 43. Dosing pump; 44. Mixing head; 45. Arrow direction; 46. B-component; 47. Injection head; 48. Recirculation tube; 49. Valve sear; 50. Upper part; 51. Arrow direction; 52. Union nut; 53. Measuring surface; 54. Arrow direction; 55. Arrow direction; 56. Arrow direction.

What is claimed is:

1. Apparatus for measuring gas charge of a liquid, comprising:
   a measuring chamber to be filled with a gas-charged liquid whose gas charge is to be measured;
   valve means for opening and closing a connection between the measuring chamber and a source of the gas-charged liquid;
   a measuring piston fitted into said measuring chamber and including a leakproof pot membrane for forming a sealed measuring space;
   a cylindrical bore provided at an upper portion of the measuring chamber opposite the valve means and;
   means for introducing pressurized air into the cylindrical bore;
   a first piston rod axially projecting from an end of said measuring piston through said measuring space towards said valve means and operative to actuate said valve means;
   a second piston rod axially projecting from a second, opposite end of the measuring piston into the cylindrical bore of the upper portion;
   a plug gage mounted at an end of the second piston rod; and
   a proximity switch mounted opposite the plug gage.

2. Apparatus according to claim 1, further comprising means for generating a counterforce to return the measuring piston to a starting position.

3. Apparatus according to claim 2, wherein said means for generating a counterforce comprises spring means.

4. Apparatus according to claim 1, wherein the proximity switch is axially adjustable.

* * * * *